United States Patent [19]

Friden et al.

[11] Patent Number: 5,032,681

[45] Date of Patent: Jul. 16, 1991

[54] **LEU3 GENE SEQUENCE OF *S. CEREVISIAE* AND USE IN REGULATION OF AMINO ACID SYNTHESIS**

[75] Inventors: Philip M. Friden, West Medford; Paul R. Schimmel, Lexington, both of Mass.

[73] Assignee: Massachusetts Institute of Technology, Cambridge, Mass.

[21] Appl. No.: 272,077

[22] Filed: Nov. 16, 1988

Related U.S. Application Data

[62] Division of Ser. No. 22,974, Mar. 6, 1987.

[51] Int. Cl.$^5$ .............................................. C07H 21/04
[52] U.S. Cl. ...................................... 536/27; 536/28; 536/29; 935/1
[58] Field of Search ............................. 536/22, 28, 29

[56] References Cited

U.S. PATENT DOCUMENTS

| | | | |
|---|---|---|---|
| 3,865,690 | 2/1975 | Okumura et al. | 195/28 R |
| 3,970,519 | 7/1976 | Tsuchida et al. | 195/29 |
| 4,421,853 | 12/1983 | Updike et al. | 435/116 |
| 4,421,854 | 12/1983 | Updike et al. | 435/116 |

OTHER PUBLICATIONS

Andreadis, et al., *Cell* 31,319–325 (Dec. 1982).
Hsu & Schimmel, *J. Biol. Chem.* 259(6), 3714–3719 (1984).
Andreadis, et al., *J. Biol. Chem.* 259(13), 8059–8062 (1984).
Brisco, et al., *Genetics* 115, 91–99 (Jan. 1987).
Kolhaw, *Amino Acid Biosynthesis and Genetic Regulation*, L. H. Hermann & R. L. Somerville, eds. 285–299 (Addison-Wesley 1983).
"LEU3 of *Saccharomyces cerevisiae* Encodes a Factor for Control of RNA Levels of a Group of Leucine-Specific Genes" Friden & Schimmel, *Mol. Cell. Biol.* 7(8), 2708–2717 (Aug. 1987).
Zhou et al., Nucleic Acids Research, vol. 15 (13), 5261–5273 (1987).

*Primary Examiner*—Johnnie R. Brown
*Assistant Examiner*—L. Eric Crane
*Attorney, Agent, or Firm*—Kilpatrick & Cody

[57] ABSTRACT

An analysis of LEU3, a leucine-specific regulatory locus encoding a factor for control of RNA levels of a group of leucine-specific genes, is provided.

DNA sequence analysis of a clone of LEU3 shows that it contains an open reading frame of 886 amino acids. There are three regions of particular interest: a cluster of acidic amino acids that are located in the C-terminal half of the coding region, a region with a repeated cysteine motif, and a region of partial homology with MATalpha2. A LEU3-dependent DNA binding activity is demonstrated to interact with homologous portions of the 5′-region of LEU1 and LEU2.

The sequencing of the LEU3 gene, and the identification of the key sequences within the gene, provide a means for producing the protein in deficient yeast strains and non-yeast strains, for modifying the gene in the key regions to thereby alter DNA binding with LEU1, and LEU2, LEU4 and other genes for proteins and expression of LEU1, LEU2, LEU4, and LEU3 gene products, and for use within other nucleotide sequences for expression in different protein frameworks. In one application, synthesis of leucine, valine, and isoleucine, as well as the expression of the enzymes specific to leucine biosynthesis, alpha-isopropyl malate synthase, IPM isomerase, and beta-IPM dehydrogenase, may be induced or enhanced.

4 Claims, 5 Drawing Sheets

(-180) CTGCGCTTTTCAAAGTTTTCAGAGCAAAAAATGAAAAGTAATGAGCACAAC-
AATAGAAGAGTATCATGATATATAAGGTCATAAAACTAGGTTTCAGGGGCT-
ATCGGCAATTTGAGGAACCTTCAACCTGCCTCAAGTAAAAATCGCTTCGTA-
ACATTAATACAAATTCTTTTTGCAATT...
ATG

| | |
|---|---|
| 1 | M E G R S D F V A T S Q S G S E M S H S E T R N R T |
| 27 | G M N A R K R K F A C V E C R Q Q K S K C D A H E R |
| 53 | A P E P C T K C A K K N V P C I L K R D F R R T Y K |
| 79 | R A R N E A I E K R F K E L T R T L T N L T S D E I |
| 105 | L K K I E E E Q E I V L D N S N F T K E K V K Q L R |
| 131 | K S A F E T T E I E P R S Y K T L R G E P I S Y S T |
| 147 | N R R H T D S S P L T L L S S S T N F D P V H S T N |
| 183 | V M T D D Q L K C L P K S L G D V Y L S S S D I A E |
| 209 | L F Q E F A T K Y H Q F L P V V D L S K G A E R I Y |
| 235 | H L S P C L F W V I L L I G L R R K F G A T D L M T |
| 261 | R L S V L V K S V L S E I T I S P I I R Y T P S D K |
| 287 | D E P V L N V A S V Y S V Q A F L L Y T F W P P L T |
| 313 | S S L S A D T S W N T I G T A M F Q A L R V G L N C |
| 339 | A G F S K E Y A S A N S E L V N E Q I R T W I C C N |
| 365 | V V S Q T V A S S F G F P A Y V S F D Y L V I S S I |
| 391 | R V P N S K S Q V D I P N E L R Q M A Q I A R F E N |
| 417 | Q I V N T M N S T P A S V T G M V S Q E E K Q P L L |
| 443 | H V L N Q Q L S Q L E I S L E E N N L D D I R K F L |
| 469 | L L V A K V H L L T Y Y F T D V T S Q S A G K S N G |
| 495 | N I Y E G S Y S I I E L D T S F E T K R G L V K V Y |
| 521 | N A A V N F L I H A N S M W E H D P T I I K Y F P G |
| 547 | L F V L N I W Q S A C I I S K L I H S S L H S M L D |
| 573 | V N S G K K A Y N N A I S L T F N A S V L K Y D M A |
| 599 | Y R S S G I M R S I W S L F A N M Y D A W K N D Q K |

(-2759)  ...TAAAGTCCTTTTCTTTTTTTGCGTAAT
GTTTACTTACCCTCGAAAAAATGTTATGTAATGACTGCGGTGCTACAGGAG
AGGTAAATGATTTTCTATATACGTTTATATTTCTTCCATTTACGCACA

FIGURE 3

| LEU1 | (-218) | C C G G G A C C G G | (-209) |
| --- | --- | --- | --- |
| LEU1 | (-188) | T C G T A A C C G G | (-179) |
| LEU2 | (-196) | C C G G A A C C G G | (-187) |
| LEU4 | (-455) | C C G G A G C G G G | (-446) |
| LEU4 | (-450) | G C G G G A C C G G | (-441) |
| ILV2 | (-466) | C C G G T A C C G G | (-457) |
| ILV2 | (-476) | C C G G A G C C T G | (-467) |

FIGURE 4

LEU3 GENE SEQUENCE OF S. CEREVISIAE AND USE IN REGULATION OF AMINO ACID SYNTHESIS

This is a divisional of application Ser. No. 022,974 filed on Mar. 6, 1987 by Philip M. Friden and Paul R. Schimme for "The LEU3 Gene Sequence of S. cerevisiae a Use in Regulation of Amino Acid Synthesis issued Sept. 26, 1989 as U.S. Pat. No. 4,870,159."

BACKGROUND OF THE INVENTION

The United States government has rights in this invention by virtue of National Institute of Health grant No GM15539.

In bacteria, operons for amino acid biosynthetic enzymes are controlled specifically by their respective end-product amino acids. In yeast, however, many of the genes encoding amino acid biosynthetic enzymes are subject to regulation by the general amino acid control system. This regulatory network consists of a hierarchy of proteins whose function is to modulate the levels of a number of amino acids in the cell. Starvation for any one of these amino acids leads to derepression of all of the genes subject to general control.

Previous studies of enzymes involved in the biosynthesis of leucine in S. cerevisiae revealed a combination of both general and specific amino acid regulation. LEU4, which encodes the first enzyme in the pathway, alpha-isopropyl malate synthase, abbreviated alpha-IPM synthase, is subject to regulation by both the general amino acid control system and specifically by leucine through feedback inhibition. LEU1 and LEU2, which encode the second and third enzymes in the pathway, respectively, are only under specific amino acid control. Expression of both genes is repressed by elevated levels of leucine. This sensitivity to a specific amino acid seems to distinguish these genes from most others that are associated with amino acid biosynthesis in yeast.

The leucine-specific control of LEU1 and LEU2 is thought to be indirect. Expression of these two genes appear to be a function of the level of alpha-IPM, the product of the first enzyme in the pathway. This is based on the following results: (1) the levels of the LEU1 and LEU2 gene products are sharply decreased in a strain that lacks a functional synthase; (2) leu1 and leu2 mutants, which are expected to accumulate intermediates in the pathway (such as alpha-IPM), exhibit increased levels of beta-IPM dehydrogenase and alpha-IPM isomerase, the products of the LEU2 and LEU1 genes, respectively; and (3) a strain that contains a feedback resistant alpha-IPM synthase and produces high levels of alpha-IPM, also has increased levels of the LEU1 and LEU2 gene products, as reported by Baichwal et. al., in *Current Genetics* 7, 369–377 (1983) and Brisco et al in *Genetics* 115, 91–99 (1987). Because alpha-IPM synthase is feedback inhibited by leucine, the levels of alpha-IPM are directly related to the levels of leucine in the cell. Accordingly, if alpha-IPM functions as an inducer, it could be responsible for the indirect, leucine-specific control of LEU1 and LEU2.

A single genetic locus having the potential for being a factor in the regulation of LEU1 and LEU2 was uncovered by analysis of mutants defective in leucine biosynthesis. This mutant allele, designated leu3, is a leaky leucine auxotroph which produces low levels of both the LEU1 and LEU2 gene products and is described by Kohlhaw in "Regulation of Leucine Biosynthesis in lower Eukaryotes", *Amino Acid Biosynthesis and Genetic Regulation*, L. H. Herrmann and R. L. Somerville, eds., 285–299 (Addison-Wesley 1983). One hypothesis is that the LEU3 gene product functions as a positive activator of LEU1 and LEU2, in conjunction with alpha-IPM as an inducer.

The nucleotide sequences of LEU1 and LEU2 have been established and it has been shown that levels of the respective mRNAs are sensitive to intracellular leucine concentrations (Andreadis et al., *Cell* 31, 319–325 (1982); Hsu and Schimmel, *J. Biol. Chem.* 259, 3714–3719 (1984); Andreadis et al., *J. Biol. Chem* 259, 8059–8062 (1984)). This work also established a section of partial nucleotide sequence homology between the 5'-regions of the two genes.

To date, the sequence of LEU3 has not been known, nor its exact role in regulation of amino acid synthesis, specifically, the interaction of the gene product of LEU3 with LEU1 and LEU2.

It is therefore an object of the present invention to provide a further characterization of the role of LEU3 in the leucine-specific regulation of the LEU1 and LEU2 genes.

It is a further object of the present invention to provide the sequence of the LEU3 gene and to define the roles of portions of the sequence involved in DNA binding and gene regulation.

It is a still further object of the present invention to provide a means for inducing or regulating protein synthesis using the product of the LEU3 gene.

SUMMARY OF THE INVENTION

Although the majority of genes for amino acid biosynthesis which have been examined are under general amino acid control, LEU1 and LEU2 respond specifically to leucine. Provided is an analysis of LEU3, a leucine-specific regulatory locus encoding a factor for control of RNA levels of a group of leucine-specific genes. LEU3 is shown to be necessary for expression of wild type levels of LEU1- and LEU2-specific RNAs. Further, the levels of LEU4-specific transcripts are affected by LEU3.

DNA sequence analysis of a clone of LEU3 shows that it contains an open reading frame of 886 amino acids. A striking feature of the predicted LEU3 protein is a cluster of acidic amino acids (19 out of 20) that are located in the C-terminal half of the coding region. The protein also has a repeated cysteine motif and a region of partial homology to MATalpha2 and the homeo box domain.

Whole cell extracts containing a LEU3-dependent DNA binding activity are demonstrated to interact with the 5'-region of LEU1 and LEU2. Subdivision of the LEU2 5'-region establishes that the LEU3-dependent binding activity interacts only with the segment of LEU2 which is homologous with LEU1.

The LEU3-dependent DNA binding activity is useful in the induction or regulation of protein synthesis including not only expression of LEU1, LEU2, and LEU4, but also any gene wherein the sequences homologous to the 5' regions of LEU1, LEU2, LEU4, and ILV2 are incorporated into the 5' region of the gene.

BRIEF DESCRIPTION OF THE DRAWINGS

FIG. 1 is a deletion analysis of the LEU3 locus. Various fragments of the LEU3 complementing plasmids pPF701 and pPF702 were cloned into yeast shuttle vectors containing 2 microns DNA and the URA3 gene. The insert sizes of pPF701 and pPF702 are 10.7 and 11.2 kbp respectively. Plasmid pPF711 was constructed by deleting a 5.5 kbp BstE11 fragment from pPF702, the result of which is to fuse a distal 1.5 kbp insert fragment to the remainder of the insert. The open rectangles represent insert DNA; vector sequences are represented by the thin lines. The hatched area corresponds to the LEU3 open reading frame. Complementation was measured in strain PDY139-11B as the ability of transformants to grow on minimal media without leucine or with 0.6 mM Tfl.

FIG. 2 is the nucleotide and deduced amino acid sequence of the LEU3 gene. The region from +20 to +2790 was sequenced on both strands. The numbering of the DNA sequence, in parentheses, is from the start of translation. The amino acids are numbered from the proposed initial methionine. The region of acidic amino acids is underlined. The region containing the repeated cysteine residues is underscored with dots. The dashed lines underscore the region of partial homology with MATalpha2 and the homeo box domain. The major transcription initiation sites, as determined by S1 mapping, are indicated by asterisks.

(A) Organization of the LEU2 upstream region. Numbering is relative to the start of translation. ORF indicates the leucine-rich open reading frame. The 5'-end of the major LEU2 transcript is indicated by the wavy arrow. The putative leucine-specific upstream activating site ($UAS_L$) is indicated by the hatched rectangle. The sizes of fragments B (170 bp) and C (114 bp) are inconsistent with the size of fragment A (279 bp) due to the filling in of 5 base "overhangs" that were generated in the cleavage of fragment A to yield fragments B and C.

(B) Analysis of LEU3-dependent protein binding to the LEU2 upstream region using the gel retardation assay. Extracts were prepared from strains PDY102-1A (LEU3) and PDY139-11B (leu3). $^{32}$p-labelled fragment A was used as substrate. F indicates free DNA. Major complexes are indicated by arrows.

(C) Analysis as in FIG. 4B except for the replacement of fragment A with fragment B or C as indicated. The amount of extract per reaction was 40 micrograms.

(D) Analysis as in FIG. 4C except that a 282 bp XbaI-ClaI fragment of the LEU1 upstream region was used as substrate.

DETAILED DESCRIPTION OF THE INVENTION

The sequence and properties of the LEU3 gene, as depicted in FIGS. 1-4, were obtained as follows:

Isolation and Initial Characterization of LEU3-Containing Plasmids

In order to select a genomic clone of LEU3 by plasmid transformation, strain PDY139-11B was constructed. The relevant genotype of this strain is leu3-781 ura3-52 LEU4$^r$-103. The product of the LEU4$^r$ allele, which is no longer subject to feedback inhibition by leucine, confers a dominant resistance to the toxic analog trifluoroleucine. Because of the low levels of the LEU1 and LEU2 gene products in leu3 strains, PDY139-11B has a leucine auxotrophy which renders the cells sensitive to trifluoroleucine. The introduction of LEU3-containing plasmids into PDY139-11B imparts both leucine prototrophy and trifluoroleucine resistance.

PDY139-11B was transformed with DNA from a yeast genomic library. This library was constructed by ligating yeast chromosomal DNA, which had been partially digested with Sau3A, into the BamHI site of the multi-copy shuttle vector YEp24 (Carlson and Botstein, Cell 28, 145-154 (1982)). The vector also carries the URA3 gene as a selectable marker. Approximately 9000 Ura$^+$ transformants were screened for either leucine prototrophy or resistance to trifluororleucine. From this screen 10 independent Leu$^+$/Tfl$^r$ transformants were obtained.

Four of the transformants were chosen for further study. Each was grown under non-selective conditions and was monitored for loss of the plasmid-borne URA3 marker and of the Leu$^+$/Tfl$^r$ phenotypes. Each of these transformants co-segregated the Ura$^+$ and Leu$^+$/Tfl$^r$ phenotypes. As an additional test that the Leu$^+$/Tfl$^r$ phenotypes are plasmid dependent, total DNA was prepared from each transformant, the plasmids were isolated by transformation of E.coli and were then reassayed by transforming strain PDY139-11B. All of the resulting Ura$^+$ transformants were also Leu$^+$/Tfl$^r$.

Dissection and Further Analysis of the LEU3 Locus

Figure 1:
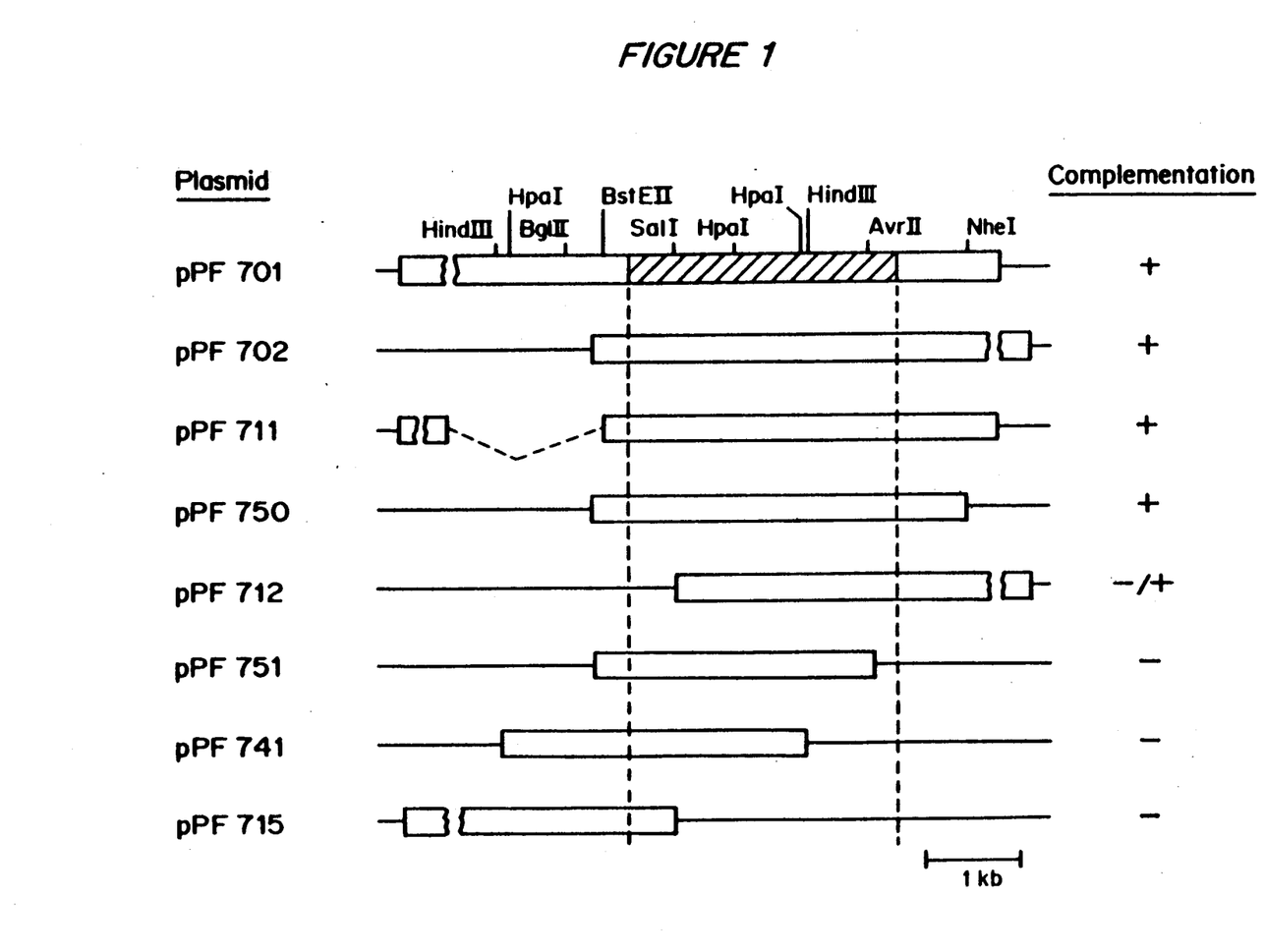

Restriction mapping of plasmid isolates identified two distinct types that are designated pPF701 and pPF702. These plasmids, which each confer Leu$^+$/Tfl$^r$ on PDY139-11B, have in common a 3.8 kbp yeast genomic DNA segment. Based on this observation, a number of deletion plasmids were constructed to further define the LEU3 locus (FIG. 1). This analysis establishes that the smallest region common to the plasmids which fully complements the leu3 allele is a 3.4 kbp segment that extends from the BstE11 site to the NheI site.

Whether cloned DNA which complements leu3 can direct integration to the LEU3 locus in the yeast chromosome was then tested. This was achieved by cloning a 4.6 kbp HindIII fragment (same as the LEU3 segment in plasmid pPF741 (FIG. 1)) into the yeast integrating vector YIp5 (Struhl et al., Proc. Nat'l. Acad. Sci. U.S.A. 76, 1035-1039 (1979)). This plasmid contains URA3 as a selectable marker but has no means for autonomous DNA replication in yeast. To direct integration to the LEU3 locus, the constructed plasmid was linearized by cleavage at the unique BstE11 site within the insert. This DNA was then transformed into a ura3-52 his5 strain designated F23. Stable Ura$^+$ transformants were crossed to PDY139-11B and the resulting diploid was sporulated and subjected to tetrad analysis.

The results, summarized in Table 1, show that the integrated URA3 gene is tightly linked to the wild type LEU3 allele. However, the heterozygous HIS5 marker in the diploid segregates randomly with respect to LEU3 and URA3. These observations suggest that the 4.6 kbp HindIII fragment contains sequences that direct integration to the LEU3 locus.

TABLE I

Cloned DNA Directs Integration at the LEU3 Locus

| Phenotypes | Number of Spores Displaying Phenotype |
| --- | --- |
| Leu$^+$Ura$^+$ | 37 |
| Leu$^+$Ura$^-$ | 0 |
| Leu$^-$Ura$^+$ | 0 |
| Leu$^-$Ura$^-$ | 41 |
| Leu$^+$His$^+$ | 19 |
| Leu$^+$His$^-$ | 18 |
| Leu$^-$His$^+$ | 21 |
| Leu$^-$His$^-$ | 20 |

The LEU3 locus has been mapped to chromosome XII. This was accomplished by hybridizing LEU3-specific probes to a blot of intact yeast chromosomes that were separated by orthogonal-field-alternation gel electrophoresis, according to the method of G. F. Carle and M. V. Olson, *Nuc. Acids Res.* 12, 5647–5664 (1984). The result is in agreement with the map position of LEU3 recently reported by P. R. G. Brisco et al., *Genetics* 115, 91–99 (1987). Brisco et al., reported the cloning of LEU3 along with preliminary genetic studies, but not the sequence. He also showed that the presence of a LEU3 plasmid clone boosts the production of LEU1 and LEU2 proteins in defective yeast cells, although not the means by which it did so.

Effect of LEU3 on the Levels of LEU1- and LEU2-Specific RNAs

The Northern blot hybridization method was used to detect LEU1- and LEU2-specific RNAs in isogenic strains that differ only at the LEU3 locus. These strains, PDY102-1A (LEU3) and PDY139-11B (leu3), contain the LEU4$^r$ allele. As a result, neither strain is feedback inhibited by leucine and therefore is unimpeded in the synthesis of alpha-IPM. The latter is proposed to be a co-factor in the induction of synthesis of the LEU1 and LEU2 gene products.

The denatured RNA was resolved on an agarose/formaldehyde gel, transferred to nitrocellulose and probed with the appropriate $^{32}$p-labeled fragment.

The results show that the level of LEU2-specific RNA is dependent on LEU3. This was the first time that it has been shown that the LEU3 gene has a direct effect on RNA levels. Introduction of the LEU3 plasmid pPF711 into a leu3 strain returns the LEU2-specific RNA to levels observed in the LEU3 strain. It is of interest that LEU3 on a multi-copy plasmid does not increase the level of LEU2 RNA substantially above that observed in PDY102-1A, which contains a single chromosomal copy of LEU3, indicating that a co-factor for LEU3 function, such as alpha-IPM, is limiting.

Similar hybridization experiments show that the level of LEU1 RNA is also dependent on LEU3.

An RNA blot was probed with DNA from the HIS3 and LEU2 genes. HIS3 is known to be controlled by the general amino acid control system. The result shows that HIS3 RNA levels are not sensitive to the nature of the LEU3 allele. This is expected if the effects of LEU3 are distinct from those of the general amino acid control system.

Effect of LEU3 on the Levels of LEU4-Specific RNA

Figure 3:
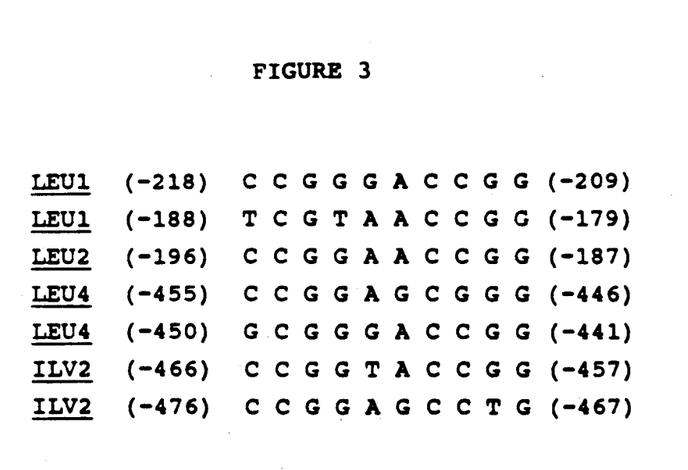
FIG. 3 is the sequence motif found in several yeast proteins implicated in gene regulation. Conserved amino acids are boxed. Gaps were introduced to account for the three extra amino acids in LEU3.

The effect of LEU3 on the transcription of LEU4 was also examined. Regulation of LEU4 expression by leucine (as opposed to feedback regulation acting on the gene product) has not previously been observed. The recently determined sequence of LEU4 contains a few regions of partial homology to those 5'-regions of LEU1 and LEU2 that are thought to be important for regulation by leucine (FIG. 3).

The results show that levels of LEU4 RNA are sensitive to the product of the LEU3 gene, although the effect is not as great as is observed with LEU1 and LEU2 RNA levels. The limited effect of LEU3 on LEU4 RNA may be related to the somewhat weaker homology of LEU4 upstream sequences with those of LEU1 and LEU2 or perhaps to the position of the sequences relative to the start of transcription.

The Cloned LEU3 Gene Restores Leucine Sensitivity to LEU1 and LEU2

LEU1 and LEU2 gene product levels are believed to be controlled through leucine-dependent alteration in the amount of alpha-IPM. Synthesis of this intermediate is catalyzed by the LEU4 gene product. To determine whether the cloned LEU3 allele confers leucine-sensitive synthesis of LEU1 and LEU2 RNA to the leu3 strain, the leu3 allele was transferred to a LEU4 Tfl$^s$ background. This strain (designated PFY400-2C), with the wild-type LEU4 allele, is subject to feedback inhibition and leucine-dependent modulation of the levels of alpha-IPM. It was transformed with plasmid pPF711 (FIG. 1). RNA was extracted from this transformed strain after it was grown in the absence or presence of 2 mM leucine. RNA blots were prepared and hybridized to LEU1-, LEU2- and URA3-specific probes.

In RNA isolated from cells grown in the presence of 2 mM leucine, the level of LEU2-specific RNA is decreased significantly. An identical pattern of regulation by leucine is seen with LEU1-specific transcripts. These results indicate that the cloned LEU3 gene confers leucine-sensitivity to the expression of both LEU1 and LEU2 RNA.

Sequence of the LEU3 Locus

Figure 2:
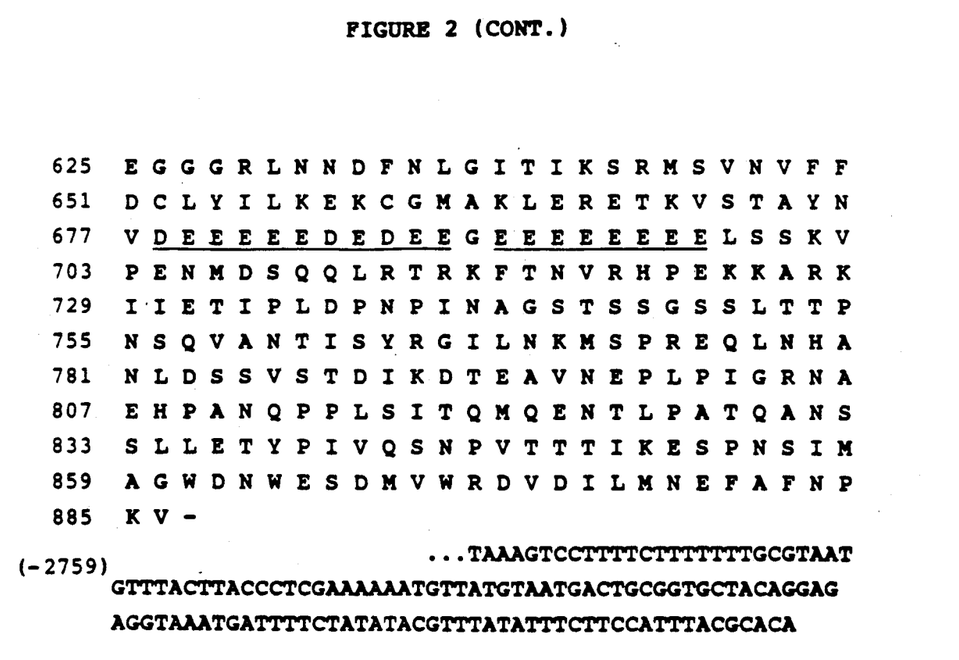

A 3 kbp region between the BstE11 and NheI sites of the LEU3 locus was sequenced by the dideoxy method of Sanger et al., *Proc. Nat'l. Acad. Sci. U.S.A.* 74, 5463–5467 (1977). Both strands of the DNA were sequenced independently. A single large open reading frame of 886 codons was found (FIG. 2). Initiation of translation at the proposed AUG would result in the synthesis of a protein with a calculated molecular weight ff 100,127 D.

The 5'-ends of the LEU3 transcripts were determined using the S1 mapping technique of Berk and Sharp, *Cell* 12, 721–732 (1977). Four major mRNA 5'-ends are located between bp −116 and −94. In addition, a few minor transcription initiation sites are located between bp −94 and −45. In all cases, the first ATG downstream from the 5'-end of the mRNA is the proposed start of translation. There do not appear to be sequences upstream of the mapped transcription initiation sites with strong homology to the TATA sequence thought to be important in eukaryotic promoters. Sequences that correspond to one of the proposed yeast termination sites are located 50 bp downstream from the UAA stop codon.

There are three distinct features of the LEU3 coding sequence. The most striking feature of the LEU3 coding region is a run of 19 out of 20 acidic amino acids, spanning codons 678 to 697 (FIG. 2), which consist mostly of glutamic acid residues. The LEU3 coding region also contains sequences homologous to two proposed DNA binding domains, a lysine rich region with a repeated cysteine motif, which is highly conserved in a few other yeast proteins thought to be involved in gene regulation, located in the amino terminal region of LEU3 (codons 37 to 67, FIG. 2) and a short stretch of amino acids with partial homology to a portion of the homeo box domain which is conserved in the MATalpha2 and MATa1 genes (codons 349 to 361, FIG. 2). While the homology in the latter case is not extensive, the conserved amino acids include those found by Porter and Smith, in *Nature* 320, 766-768 (1986), to be essential for both haploid and diploid functions in MATalpha2.

LEU3-Dependent DNA Binding Activity

The possibility that a LEU3-dependent product is a regulatory protein by virtue of interactions with the 5'-regions of LEU1 and LEU2 was then examined. Extracts from a LEU3 strain were compared to those from leu3 cells to test for a LEU3-dependent DNA binding activity that recognizes the upstream regions of LEU1 and LEU2. The gel retardation technique, which can detect protein-DNA complexes because the mobility of a DNA fragment in a polyacrylamide gel is shifted upon protein binding, as described by Fried and Crothers, *Nuc. Acids Res.* 9,6505-6525 (1981) and Garner and Revzin, *Nuc. Acids Res.* 9, 3047-3060 (1981), was used. The extent of the shift depends on the number of bound proteins and their molecular mass.

Cell extracts for binding experiments were prepared from strains PDYI102-1A (LEU3) and PDY139-11B(leu3). A HincII fragment of 279 bp that extends from −405 to −126 (FIG. 4A, fragment A) was used to examine binding to the LEU2 upstream region. The fragments are numbered with respect to +1 as the start of the coding region. This fragment contains the region of homology with LEU1. After combining the end-labeled DNA with the extracts, the resulting complexes were separated on a 4% non-denaturing polyacrylamide gel. The experiments were done in the presence of a 2000-fold excess of sonicated salmon sperm DNA to eliminate non-specific complexes.

Both extracts give rise to two distinct complexes, although the gel migration patterns of these complexes are different. The amount of the major complex detected with the LEU3 extracts is much greater than that of the corresponding complex seen when extracts from leu3 cells are used. However, a smaller (faster migrating) complex is seen in the leu3 lane, suggesting that a binding protein present in the LEU3 extracts is absent or decreased in size. In addition, a large complex seen with increased amounts of the LEU3 extracts is not detected with the leu3 extracts. The intensity of all of the bands observed is dependent on the amount of protein extract added to the binding reaction.

Figure 4:
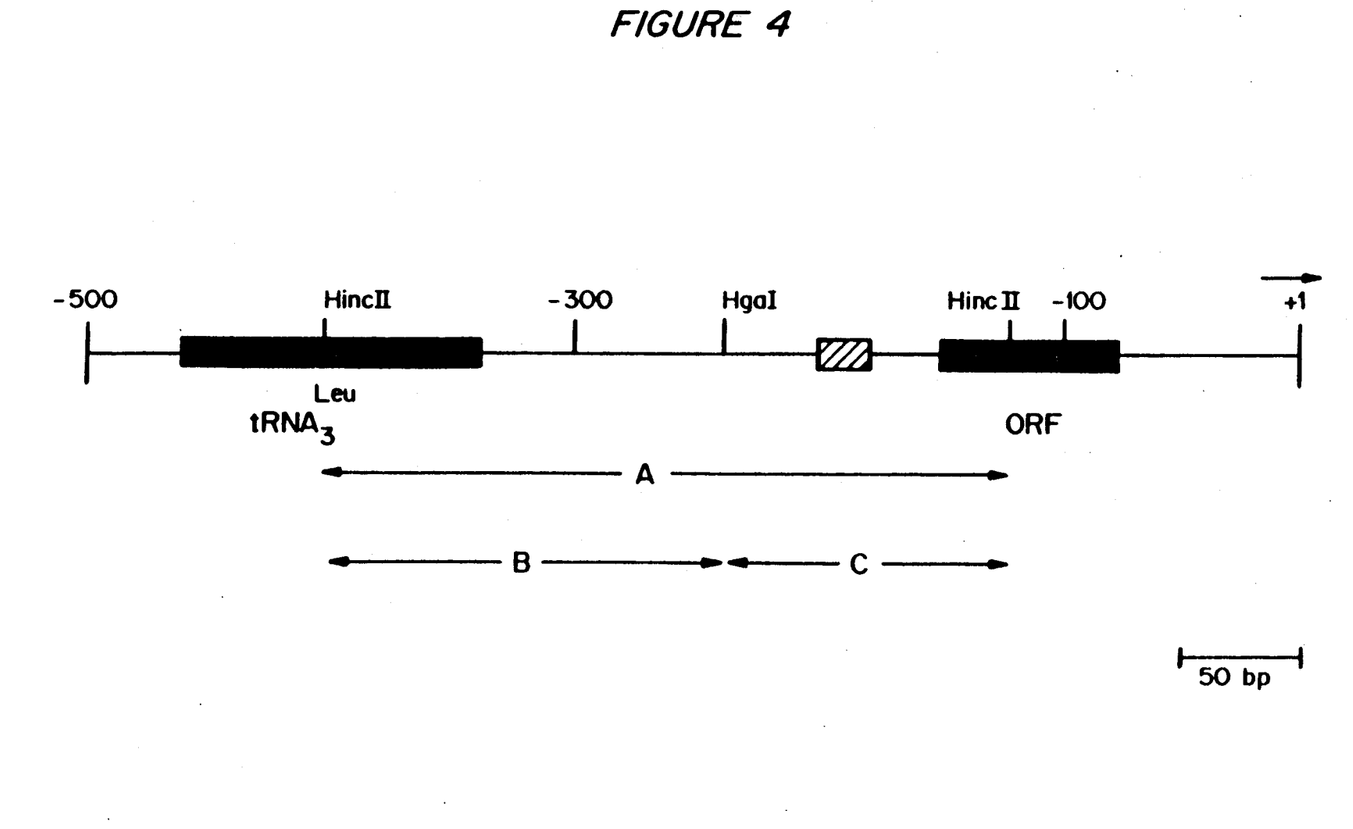
FIG. 4 is a diagram of the LEU3-dependent protein binding to the upstream regions of LEU1 and LEU2.

FIG. 4 shows the results of experiments which define more precisely the location of the 5'-region of LEU2 which interacts with the LEU3-dependent DNA binding activity. The 279 bp HincII fragment was cleaved with HgaI to generate two fragments that are designated B (170 bp) and C (114 bp). Fragment C contains the region of LEU2 with partial homology with the 5' region of LEU1. Only fragment C forms complexes that are dependent on LEU3. The intensity of the bands observed with fragment C is decreased by the addition of unlabeled fragment A.

Experiments were also conducted with a DNA fragment from the 5'-region of LEU1. This 282 bp fragment extends from −309 to −27. The pattern of LEU3-dependent complex formation is similar to that observed with the LEU2 DNA fragments.

The sequencing of the LEU3 gene, the identification of the key sequences within the gene, and the characterization of a LEU3 dependent binding activity provide a means for producing the LEU3 gene product in deficient yeast strains and non-yeast strains, for inducing and regulating the expression of the gene products of LEU1, LEU2, LEU4, ILV2 and other leucine-specific proteins through binding of the homologous sequences with the LEU3 dependent binding activity, and for use in controlling expression of other proteins by incorporating the homologous sequences into the 5' region of the gene encoding the protein to be expressed and then interacting the gene with the LEU3 dependent binding activity. One application that follows is the induction or enhancement of the synthesis of leucine, valine, and isoleucine, as well as the expression of the enzymes specific to their biosynthesis, alpha-isopropyl malate synthase, IPM isomerase, and beta-IPM dehydrogenase.

Materials and Methods

Strains and Genetic Methods

The following yeast strains were used: PDY139-11B (alpha LEU4$^r$-103 leu3-781 ura3-52), Peter Drain, Massachusetts Institute of Technology, Cambridge, Mass.; PDYI102-1A (a LEU4$^r$-103 ura3-52), Peter Drain, MIT; F23 (a his5 ura-52), Peter Drain, MIT; PFY400-2C (alpha his5 ura3-52 leu3-781), a segregant derived from the cross F23 X PDY139-11B. Yeast growth media were prepared and general yeast methods performed as described by Sherman et al., *Methods in Yeast Genetics* (Cold Spring Harbor Laboratory, Cold Spring Harbor, N.Y. 1979). Yeast were transformed by the method of A. Hinnen et al., *Proc. Nat'l. Acad. Sci. U.S.A.* 75, 1929-19331978) or H. Ito et al., *J. Bacteriol.* 41, 459-472 (1983).

The bacterial strains HB101 and JM101 were used for maintaining pBR322- and M13-derived plasmids, respectively. Bacterial methods were as described R. W. Davis et al., *Advanced Bacterial Genetics* (Cold Spring Harbor Laboratory, Cold Spring Harbor, N.Y. 1980).

Hybridization Procedures

Yeast RNA for Northern hybridization was prepared as described by Carlson and Botstein, Cell 28, 145-154 (1982). RNA's were resolved on agarose/formaldehyde gels as described by Maniatis et al., *Molecular Cloning* (Cold Spring Harbor Laboratory, Cold Spring Harbor, N.Y. 1982) except that the gels were run in 10 mM NaPO$_4$ buffer (pH 7.0) and blotted directly after washing in sterile double distilled H$_{2O}$.

Yeast DNA for chromosome blots was prepared as described by Schwartz and Cantor (1984). Orthogonal-field-alteration gels were run and blotted to nitrocellulose as described by Carle and Olson *Nuc. Acids Res.* 12, 5647-5664 (1984).

Pre-hybridization and hybridization conditions were as follows: 50% formamide, 5X SSPE, 5X Denhardts solution and 0.5% SDS at 37° C. DNA probes (10$^7$ cpm) labeled by nick translation according to the method of Maniatis et al., *Molecular Cloning* (1982) were incubated with the filter for 12 hours. The final wash for all blots was 0.1X SSPE 0.1% SDS at 37° C. (55° C. for chromosome blots).

Plasmid Constructions

The details of the plasmid constructions are as follows: pPF711, deletion of 5.5 kbp BstE11 fragment from plasmid pPF701; pPF712, deletion of SalI fragment from pPF702 which extends leftward from the insert SalI site to a SalI site in adjacent vector sequences; pPF715, deletion of a SalI fragment from pPF701 which extends rightward from the insert SalI site to a SalI site in the adjacent vector sequences; pPF741, insertion of the 4.6 kbp HindIII fragment of pPF701 into the HindII site of plasmid YIp5 (Struhl et al., *Proc. Nat'l. Acad. Sci. U.S.A.* 76, 1035-1039 (1979)), followed by the insertion of the EcoR1 fragment of YEp24 (Botstein et al., 1979) containing the 2 micron replication functions into the unique vector EcoR1 site; pPF750, deletion of an NheI fragment from pPF702 which extends from the insert NheI site rightward to an NheI site in the adjacent vector sequences; pPF751, plasmid pPF750 was digested with both NheI and AvrII (which have complementary "overhangs") and re-ligated to delete the region between the two sites.

DNA Sequence Analysis

Large fragments of plasmids pPF701 and pPF702 were cloned into the M13 vectors mp18 and mp19. The DNA inserts were sequenced by the chain termination method of Sanger et al., *Proc. Nat'l. Acad. Sci. U.S.A.* 74, 5463-5467 (1977) as modified for [alpha-$^{35}$S]dATP by Biggin et al., *Proc. Nat'l. Acad. Sci. U.S.A.* 80, 3963-3965 (1983). DNA sequence information was initially obtained using commercially available sequencing primers (obtained from New England Biolabs). Extended stretches of DNA were sequenced by synthesizing additional sequencing primers with a Microsyn-1450A automated DNA synthesizer (Systec, Inc., Minneapolis, Minn.)

Gel Retardation Assays

Yeast extracts were prepared and assays performed as described by Arcangioli and Lescure, *EMBO J.* 4, 2627-2633 (1985). Complexes were separated on 4% polyacrylamide gels run with 0.5X TBE buffer. The DNA fragments used as substrates were purified from 4% polyacrylamide gels by electroelution and labeled with $^{32}$P using polynucleotide kinase or Klenow enzyme (large fragment, DNA polymerase 1).

Although the present invention has been described with reference to specific embodiments, variations and modifications of the disclosed sequences and protein or polypeptides regulating the synthesis of leucine-specific amino acids will be obvious to those skilled in the art. For example, the substitution of one or two nucleotides for one of the listed nucleotides in the sequences regulating binding of the protein would be obvious to those of reasonable skill in molecular genetics and protein synthesis. It is intended that such modifications and variations will fall within the scope of the appended claims.

We claim:

1. A synthetic or recombinant nucleotide sequence comprising nucleotides encoding the amino acid sequence:

D E E E E E D E D E E G E E E E E E E, wherein the amino acid sequence binds to DNA required for expression of genes selected from the group consisting of LEU1, LEU2, and LEU4.

2. A synthetic or recombinant nucleotide sequence comprising nucleotides encoding the amino acid sequence:

C V E C R Q Q K S K C D A H E R A P E P C T K C A K K N V P C, wherein the amino acid sequence binds to DNA required for expression of genes selected from the group consisting of LEU1, LEU2, and LEU4.

3. A synthetic or recombinant nucleotide sequence comprising nucleotides encoding the amino acid sequence:

N S E L V N E Q I R T W I, wherein the amino acid sequence binds to DNA required for expression of genes selected from the group consisting of LEU1, LEU2, and LEU4.

4. A synthetic or recombinant nucleotide sequence for initiation of transcription of LEU3 comprising a nucleotide sequence selected from the group consisting of:

CATGATATAT, AAGGTCAT, and AAAACTAGG.

* * * * *